United States Patent
Kennedy

Patent Number: 5,488,944
Date of Patent: Feb. 6, 1996

[54] SURGICAL DRAPE SUPPORT

[76] Inventor: Thomas M. Kennedy, 31 Esplande St., Selkirk, N.Y. 12158

[21] Appl. No.: 286,551

[22] Filed: Aug. 5, 1994

[51] Int. Cl.[6] ............................. A61M 15/00; A62B 9/00
[52] U.S. Cl. ................. 128/202.18; 128/207.14; 128/207.17; 128/DIG. 26
[58] Field of Search .................... 128/857, 858, 128/859, 863, 849, 850, 851, 852, 853, 854, 855, 856, 846, 845, 202.18, 200.24, 207.14, 207.17, 912, DIG. 26, 847, 910, 909, 914

[56] References Cited

U.S. PATENT DOCUMENTS

| | | | |
|---|---|---|---|
| 3,403,677 | 10/1968 | Struve | 128/849 |
| 3,464,411 | 9/1969 | Martinez | 128/202.18 |
| 3,482,571 | 12/1969 | Behlendt | 128/202.18 |
| 3,859,993 | 1/1975 | Bitner | 128/200.24 |
| 3,877,691 | 4/1975 | Foster | 128/200.24 |
| 3,881,477 | 5/1975 | Von Otto | 128/200.24 |
| 4,223,669 | 9/1980 | Morlidge | 128/849 |
| 4,248,218 | 2/1981 | Fischer | 128/910 |
| 4,321,917 | 3/1982 | Campbell | 128/200.24 |
| 4,377,161 | 3/1983 | Whitt | 128/200.24 |
| 4,739,753 | 4/1988 | Brehm | 128/849 |
| 4,770,169 | 9/1988 | Schmoegner | 128/910 |
| 5,033,464 | 7/1991 | Dlcastilho | 128/910 |
| 5,140,997 | 8/1992 | Glassman | 128/857 |
| 5,159,938 | 11/1993 | Laughlin | 128/857 |
| 5,195,512 | 3/1993 | Raiso | 128/200.24 |
| 5,220,699 | 6/1993 | Farris | 128/200.24 |
| 5,220,915 | 6/1993 | Troy et al. | 128/200.24 |

*Primary Examiner*—Robert A. Hafer
*Assistant Examiner*—Michael O'Neill
*Attorney, Agent, or Firm*—Heslin & Rothenberg

[57] ABSTRACT

A surgical drape support useable for oxygen supply and carbon dioxide sampling of a surgery patient includes a support member having a first and second end capable of being attached across the mouth of a patient affixing the first and second ends thereof on each side of the patient's face to create a space between the patient's mouth and the central portion of the support member. An oxygen supply hose is attached to the support member and has one or more openings therein to allow oxygen to escape therefrom. A carbon dioxide sampling hose is attached to support member and has one or more apertures therein for receiving the breath of a patient. The one or more openings in the oxygen supply hose and one or more apertures in the carbon dioxide sampling hose are located on the first side of the support to allow the support member to be attached to across the mouth of a patient so that the one or more apertures and one or more openings on the first side are facing the patient's mouth and nose.

9 Claims, 2 Drawing Sheets

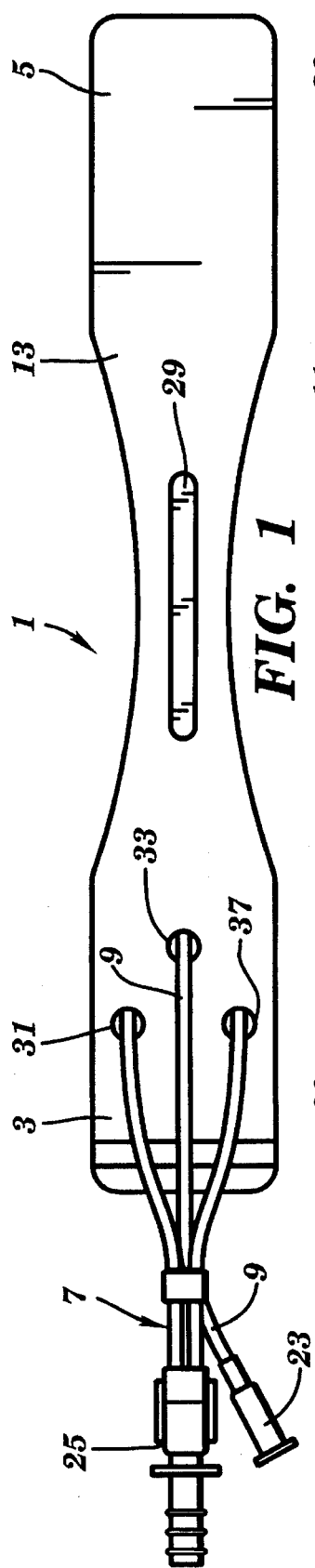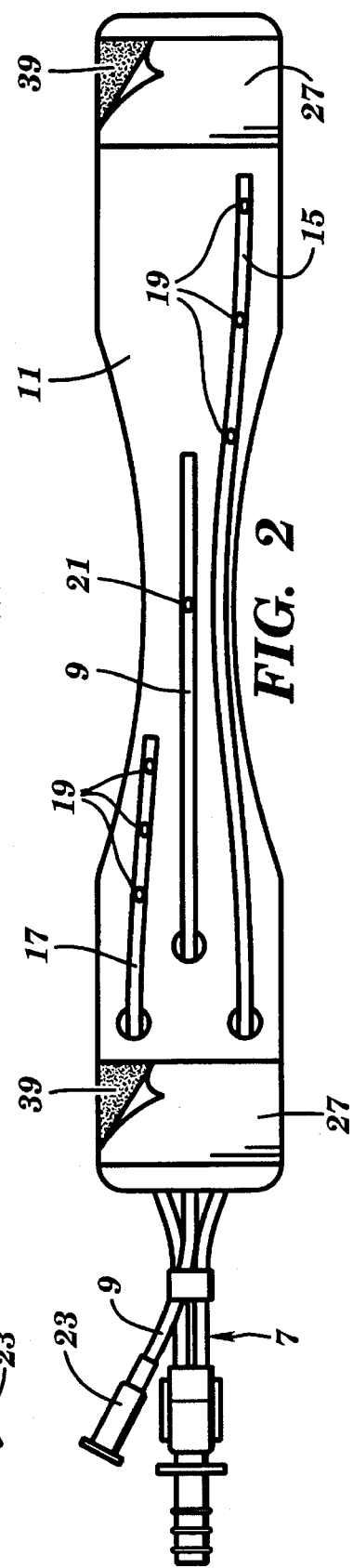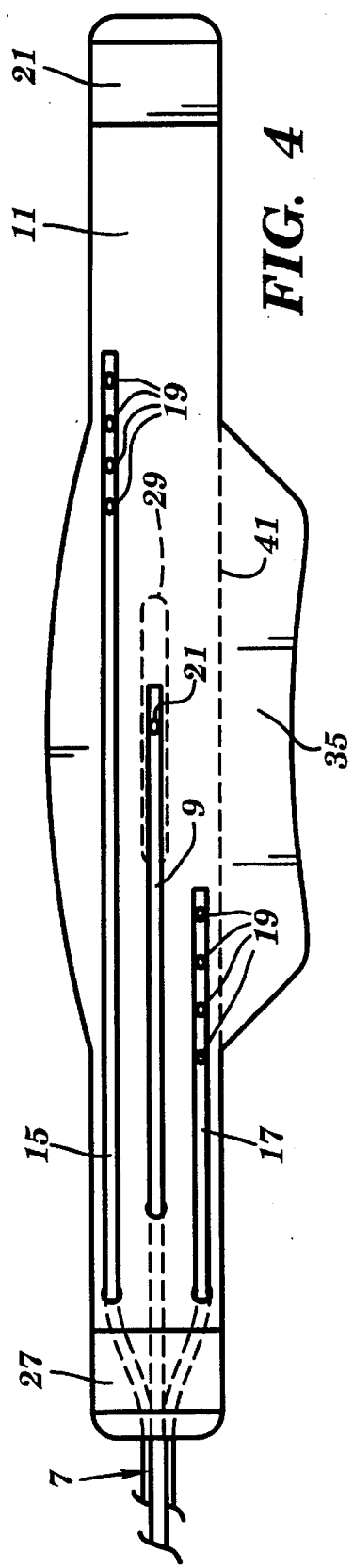

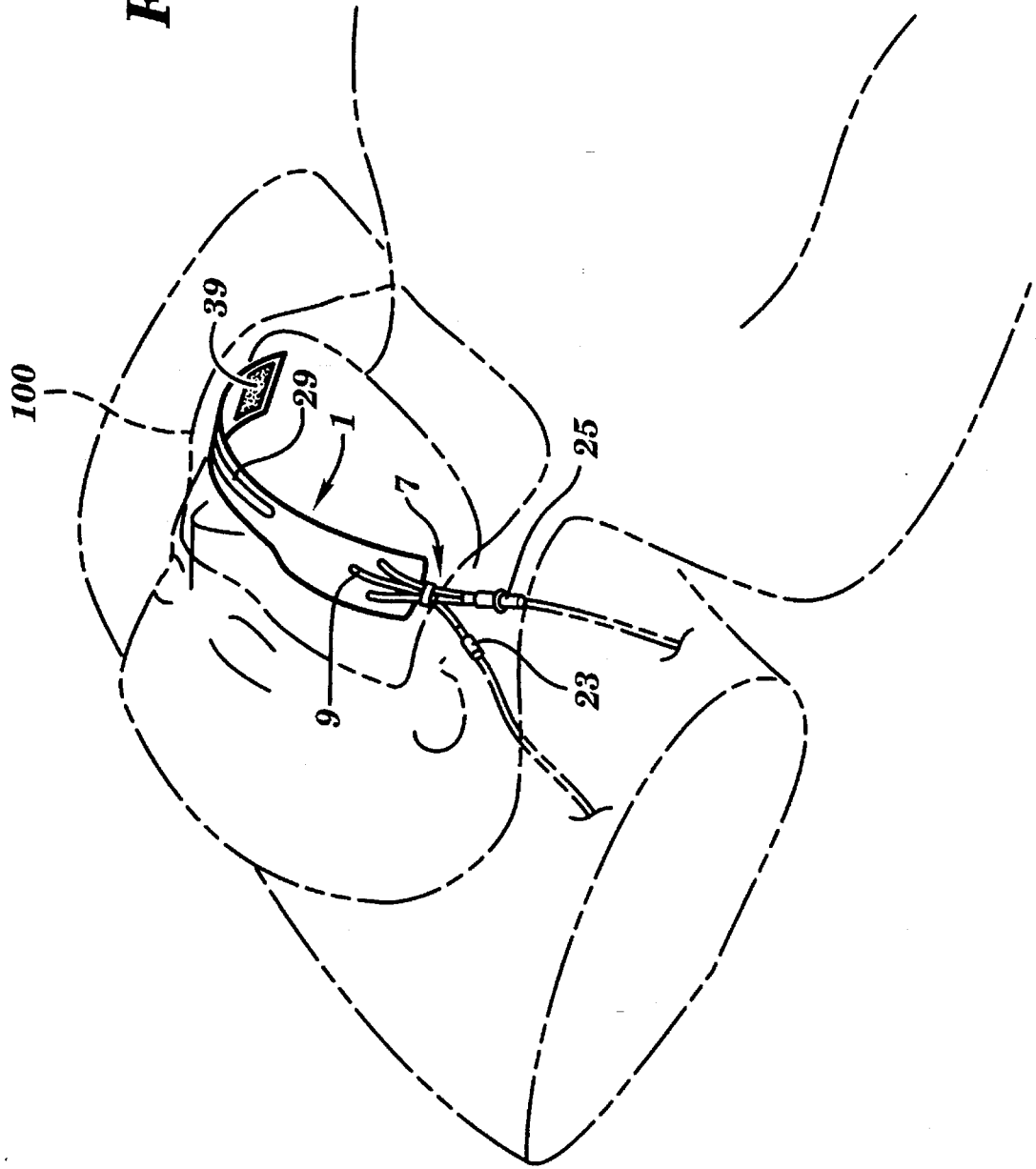

SURGICAL DRAPE SUPPORT

BACKGROUND OF THE INVENTION

This invention relates to the field of medical devices, more particularly, the invention relates to a surgical drape support useable for oxygen supply and carbon dioxide sampling.

In surgery of the upper facial area, particularly eye surgery, a drape is placed over the face of a patient. Usually the drape is supported by a drape support which also allows the drape to cover the patient's face while allowing the patient to breathe. One of the most common drape support is typically affixed to the patient's face by adhering the ends thereof to the cheeks on each side of the patient's mouth. This drape support is in the form of a flexible non-corrugated cardboard strip having adhesive ends thereto which allow the drape support to be adhered to the patient's face. A drape is placed over the drape support to create a space between the patient's face and the drape thereby allowing the patient to breathe. Moreover, the drape protects the face, including the patient's nose and mouth, from surgical debris. The drape and drape support, however, make it impractical to place an oxygen mask over the patient's mouth and/or nose. Therefore, it is not easy to provide a patient with additional oxygen or air to breathe while the patient is draped. An oxygen supply tube can be typically taped to the side of a patient's mouth, which is covered by the drape, to supply the patient with sufficient oxygen for breathing.

Additionally, the patient's carbon dioxide level should be monitored to insure that the patient's anesthesia level and respiration are sufficient. Research has indicated that under surgical drapes, carbon dioxide levels can increase significantly, cause rebreathing of exhaled carbon dioxide, increased blood levels of $CO_2$ followed by a change in a patient's mental status. In the past, monitoring the patient's respiration by sampling the level of carbon dioxide exhaled by the patient has been difficult. The standard of care would be to measure the carbon dioxide level of the patient. This is typically sampled by measuring continuous end-tidal crude method of $ETCO_2$ sampling is affixing a tube to the chin, mouth or below the nostrils of a patient to allow the breath of the patient to be received therein. The sampling tube leads to a sampling machine which measures the $ETCO_2$ level within the patient to help direct the level of anesthesia or aid in the detection of respiratory abnormalities including alveolar hypoventilation, apnea and/or obstruction.

The anesthesiologist is often faced with the problem of affixing and maintaining an oxygen supply tube and a carbon dioxide sampling tube to a patient's face. Preferably, these tubes should be placed near the patient's nostrils and/or mouth which are covered by a drape and may be partially obstructed by a drape support. However, it is often difficult and cumbersome to affix the oxygen supply tube and $ETCO_2$ sampling tube to the patient's face. Nevertheless, it is necessary to maintain the supply of oxygen to the patient and to continue sampling the patient's carbon dioxide level.

It is therefore desirable to provide a drape support which facilitates the supply of oxygen to a patient.

It is also an object of the present invention to provide a drape support which facilitates the monitoring of carbon dioxide levels of a patient.

It is also an object of the present invention to provide a drape support which facilitates both the supply of oxygen to a patient and the monitoring of carbon dioxide levels to a patient while effectively supporting the drape over a patient's face.

It is also an object of the present invention to provide a drape support which can also provide a means for supplying oxygen to a patient and for measuring the levels of carbon dioxide from a patient's breath.

SUMMARY OF THE INVENTION

The aforementioned objectives may be achieved by a surgical drape support useable for oxygen supply to and carbon dioxide sampling of a surgery patient. The surgical drape support includes a support member having a first and second end capable of being attached across the mouth of a patient by affixing the first and second ends of the support member on each side of the patient's face wherein a space is created between the patient's mouth and a central portion of the support member. An oxygen supply hose is attached to the support member and has one or more openings therein to allow oxygen to escape therefrom. A carbon dioxide sampling hose is attached to the support member and has one or more apertures therein for receiving the breath of a patient. The one or more openings in the oxygen supply hose and the one or more apertures in the carbon dioxide sampling hose may be located on a first side of the support member to allow the support member to be attached across the mouth of a patient wherein the one or more apertures and the one or more openings on the first side are facing towards the patient's mouth and the first end of the carbon dioxide supply hose may extend past the first end of the support member.

The oxygen supply hose may include an oxygen source connection at a first end thereof to operatively engage the oxygen supply hose to an oxygen source. The carbon dioxide sampling hose may include a carbon dioxide sampling connection at a first end thereof to operatively engage the carbon dioxide sampling hose to a carbon dioxide sampling machine. The oxygen supply hose may extend over a central portion of the drape support to a first end of the support member and the first end of the oxygen supply hose may extend past the first end of the support member. The carbon dioxide sampling hose may extend from the central portion of the support member to the first end of the support member and the first end of the carbon dioxide supply hose may extend past the first end of the support member.

The oxygen supply hose may include one or more branches. The first branch of the oxygen supply hose may contain one or more apertures therein and a second branch of the second supply hose contain one or more apertures therein. The one or more apertures in the first branch may be located at a first half section of the support member and the one or more apertures in the second branch may be located at a second half section of the support member.

The carbon dioxide sampling connection may comprise a Lure-Loc™ connection. The first end and second end of the drape support may each include an adhesive section capable of adhering to a patient's skin. The adhesive sections may be covered by a removable or peel-off material.

The oxygen supply hose and/or carbon dioxide sampling hose may be attached to the support member by extending one or more of the hoses through one or more apertures within the support member.

The drape support may include a flap extending from a support member. The flap may be capable of folding towards the chin of a patient when the support member is attached across the patient's mouth. This flap may rest on the patient's chin giving additional stability to the drape support and further defining the space created between the patient's mouth and central portion of the support member.

The drape support may comprise an elongate bendable material including non-corrugated cardboard. A tab may be located on the second side of the support member at a central portion thereof for preventing the support member from folding or creasing.

BRIEF DESCRIPTION OF THE DRAWINGS

The invention may best be described with reference to the detailed description herein when read in conjunction with the drawings in which:

FIG. 1 depicts top view of the surgical drape support constructed in accordance with the principles of the present invention;

FIG. 2 depicts a bottom view of the surgical drape support depicted in FIG. 1;

FIG. 3 depicts a surgical drape support such as that shown in FIG. 1 constructed in accordance with the principles of the present invention and affixed to the face of a patient without a drape supported thereon and shown in phantom; and FIG. 4 depicts a top view of an alternative embodiment of the surgical drape support constructed in accordance with the principles of the present invention.

DETAILED DESCRIPTION OF A PREFERRED EMBODIMENT

Referring to FIGS. 1 and 2, a surgical drape support constructed in accordance with the principles of the present invention is shown. The drape support includes an elongate bendable support member 1 having a first end 3 and a second end 5. One or more oxygen supply hoses 7 extend along a partial length of the support member 1. Similarly, a carbon dioxide sampling hose 9 also extends lengthwise along a portion of the support member 1.

The support member 1 may be both elongate and bendable in order to be arcuately shaped when affixed to the face of a patient as shown in FIG. 3. Such a support member may be constructed of a material, for example, non-corrugated cardboard, which is flexible enough to bend over a patient's face yet strong enough to support the weight of a surgical drape thereon. The support member may be constructed from sheets of non-corrugated cardboard having a thickness which insures that the support member maintains the requisite strength to support a surgical drape and the flexibility to be arcuately bent while affixed to the face of a patient. Alternatively the support member may be substantially arcuately shaped before being placed on the face of a patient. Such a construction could minimize the degree of bendability that the support member must exhibit in order to be attached to a patient's face.

When affixed on the face of a patient during use, a first side 11 of the support member faces the nose and/or mouth of a patient. The oxygen supply hose 7 may contain a plurality of branches including a first branch 15 and a second branch 17. The oxygen supply hose 7 may contain one or more openings 19 therein located on the first side 11 of the support member 1. The plurality of openings 19 which may be located on each of the branches 15, 17 should be oriented to face in the direction of the nose and/or mouth of a patient when the support member 1 is affixed to the face of a patient. Such a direction is typically normal to the first side 11 of the support member 1. As shown in FIGS. 1 and 2, the oxygen supply hose 7 and branches thereof 15, 17 extend along the length of the support member 1. The plurality of openings 19 may be spaced along the one or more oxygen supply hoses 7 or branches thereof 15, 17 to disperse oxygen along a wide area. This may be accomplished by utilizing a plurality of openings 19 on the first branch 15 of the oxygen supply hose 7 which are located at a first half of the first side 11 of the support member 1 and additional openings 19 may be located within the second branch 17 of the oxygen supply hose 7 at a second half of the first side 11 of the support member 1. The oxygen supply hose 7 may extend over the first end 3 where it is affixed to an oxygen source connection 25 which enables the oxygen supply hose to be operatively engaged with an oxygen supply means such as an oxygen supply tank or a hose extending therefrom (not shown).

A carbon dioxide sampling hose 9 also extends along the length of the support member 1 and is attached to the first side 11 of the support member 1. An aperture 21 may be located on the carbon dioxide sampling hose 9 preferably facing a direction normal to the first side 11 of the support member 1. When the support member 1 is affixed to face of a patient as shown in FIG. 3, the breath of the patient passes through aperture 21 into the carbon dioxide sampling hose 9 where it travels to a carbon dioxide sampling machine. Aperture 21 of the carbon dioxide sampling hose 9 is preferably located at a central portion of the support member 1 midway between the first end 3 and second end 5 thereof. At the opposite end of the carbon dioxide sampling hose 9, a means for connecting the sampling hose to a carbon dioxide sampling machine may be located. As shown in FIG. 1, a LURE-LOC connection 23 may be affixed to the second end of the carbon dioxide sampling hose 9 as a means for connecting the carbon dioxide sampling hose 9 to a carbon dioxide sampling device. The carbon dioxide sampling device typically contains a hose extending therefrom having the male section of a LURE-LOC connection while the carbon dioxide sampling hose 9 should contain the female section connected thereto. The oxygen supply hose 7 and carbon dioxide sampling hose 9 may be made of flexible clear plastic tubing currently used in the medical industry.

The carbon dioxide sampling hose 9 and/or oxygen supply hose 7 may be affixed to the support member 1 by any suitable means such as gluing or taping. However, the invention is not limited to any one particular means. Additionally, perforations or apertures 31, 33, 37 may be located within the support member 1 for extending the oxygen supply hose 7 and/or carbon dioxide sampling hose 9 therethrough to allow the hoses 7, 9 to be located on the first side of the support member 1 towards the central portion thereof. The perforations or apertures 31, 33, 37 also allow the hoses 7, 9 to be located on the second side above the first end 3 of the support member 1 so that the first side 11 of the first end 3 of the support member 1 may be adhered directly to the face of a patient without obstruction from the oxygen supply hose 7 and/or carbon dioxide sampling hose 9.

The first end 3 and the second end 5 of the support member 1 may have an adhesive medium 39 thereon for allowing the support member 1 to be adhered to the face of a patient as shown in FIG. 3. The adhesive material should be located on the first side 11 of the support member 1 and may be covered by a removable or peel-off material 27 such as paper which may be removed prior to adhering the first and second ends 3, 5 of the support member 1 to the face of the patient. Located on the second side 13 of the support member 1 at the central portion thereof may be a rigid or semi-rigid tab 29 (FIG. 1). The tab functions to prevent the support member 1 from folding at the central portion thereof and maintaining the support member 1 in an arcuate shape when affixed to the face of a patient as shown in FIG. 3. The tab may be made of any suitable semi-rigid material which prevents the support member 1 from folding including metals. The tab 29 may be affixed to the second side 13 of the support member 1 by any suitable means such as glue, tape or the like.

Referring to FIGS. 2 and 3, the surgical drape support constructed in accordance with the principle of the present invention is used by bending the support member and affixing the first and second ends 3, 5 thereof to a patient's face at each side of the patient's mouth. The first side 11 of the support member 1 should be facing the patient's face so that the apertures 19 of the oxygen supply hose 7 and aperture 21 of the carbon dioxide sampling hose 9 are exposed towards the face of the patient. The adhesive media 39 at the first and second ends 3, 5 of the first side 11 of the support member 1 may be adhered to the patient's face by peeling off the material 27 and pressing the first side 11 of the first and second ends 3, 5 of the support member 1 on the face of a patient. A hose from an oxygen source may be connected to the oxygen source connection 25 to allow oxygen to flow through the one or more oxygen supply hoses 7 out of apertures 19 for supply to a patient. Also, a carbon dioxide sampler may be connected to the carbon dioxide sampling hose 9 via the carbon dioxide sampling connection means such as the LURE-LOC connection 23 by inserting of the male section of the LURE-LOC connection affixed to the carbon dioxide sampling device to the female section of the LURE-LOC connection 23. A drape 100 is placed over the drape support to protect the nose, mouth and surrounding facial area of a patient so that surgery may be performed at the upper facial area including the eyes of a patient. Alternatively, the ends of the support member 1 may be taped to a patient's face by use of surgical tape.

Referring to FIG. 4, an alternative embodiment of the surgical drape support constructed in accordance with the principles of the present invention is shown. In this embodiment, a flap 35 extends from the central portion of the support member 1. A fold or perforations 41 may be located on the support member to allow the flap 35 to be bent relative to the remaining portion of the support member 1. When used on a patient, the flap may be located towards the chin of a patient and folded towards the chin to create a cavity. The patient may, therefore, breathe into the cavity and oxygen is supplied into the cavity. Also, carbon dioxide from the patient is exhaled into the cavity and sampled by the carbon dioxide sampling machine via the carbon dioxide sampling hose 9. The flap 35 helps maintain the drape support on the patient's chin while giving the drape support added strength to support a drape. Also, the flap 35 forms a closed cavity where oxygen will flow therein thereby increasing inspired oxygen concentration the patient will breathe in. As a result, the increasing blood oxygen levels add a measure of safety while the patient is sedated. By having oxygen flow into the cavity formed by the flap 35, excess carbon dioxide that the patient exhales could be blown out of the cavity.

Although the invention has been disclosed in conjunction with the embodiments depicted herein, it will be apparent to one of ordinary skill in the art that various modifications may be made to the invention without departing from the scope of the invention as defined by the following claims.

What is claimed is:

1. A combination of a surgical drape and a drape support, said combination adapted to fit a patient placed upon an operating table and useable for surgery of upper facial area, oxygen supply to and carbon dioxide sampling of a surgery patient, said combination comprising:

an elongate support member, having a first end and a second end, adapted to extend only across a patient's mouth;

means for affixing said first and second ends of said elongate support member on each side of a patient's face wherein a space is created between the patient's mouth and a central portion of said elongate support member so that said elongate support member does not cover the patient's eyes and nose;

a drape placed upon said elongate support member such that a gap is created between a patient's face and the drape wherein the drape covers a patient's nose and the patient's mouth while allowing surgery to be performed on a patient's upper facial area;

an oxygen supply hose extending through and along said elongate support member, said oxygen supply hose having at least one opening therein to allow oxygen to escape therefrom;

a carbon dioxide sampling hose extending through and along said elongate support member, said carbon dioxide sampling hose having at least one aperture therein for receiving the breath of a patient; and said at least one opening in said oxygen supply hose and said at least one aperture in said carbon dioxide sampling hose being located on a first side of said elongate support member to allow the support member to be attached across the mouth of a patient wherein said at least one aperture and said at least one opening on said first side are adapted to face towards a patient's mouth.

2. A combination of a surgical drape and drape support, said combination adapted to fit a patient placed upon an operating table and useable for surgery of upper facial area, oxygen supply to and carbon dioxide sampling of a surgery patient, said combination comprising:

an elongate support member having a first end and a second end adapted to extend only across a patient's mouth;

means for affixing said first and second ends of said elongate support member on each side of a patient's face wherein a space is created between the patient's mouth and a central portion of said elongate support member so that said elongate support member does not cover the patient's eyes and nose;

a drape placed upon said elongate support member such that a gap is created between a patient's face and the drape wherein the drape covers a patient's nose and the patient's mouth while allowing surgery to be performed on a patient's upper facial area;

an oxygen supply hose extending through and along said elongate support member, said oxygen supply hose comprising a plurality of branches, wherein a first branch contains at least one opening therein and wherein a second branch contains at least one opening therein to allow oxygen to escape therefrom, each branch of said plurality of branches of said oxygen supply hose extending over a central portion of said elongate support member to said first end of said elongate support member, said oxygen supply hose having a first end extending past the first end of said elongate support member, and further comprising an oxygen source connection at said first end of said oxygen supply hose to operatively engage said oxygen supply hose to an oxygen source;

a carbon dioxide sampling hose extending through and along said elongate support member and having at least one aperture therein for receiving the breath of a patient, said carbon dioxide sampling hose extending from said central portion of said elongate support member to the first end of said elongate support member and having a first end extending past the first end of said elongate support member, said carbon dioxide sampling hose comprising a carbon dioxide sampler connection at the first end thereof to operatively engage said carbon dioxide sampling hose to a carbon dioxide sampling machine; and said at least one opening in said first branch and said at least one opening in said second branch of said oxygen supply hose and said at least one aperture in said carbon dioxide sampling hose being located on a first side of said elongate support member to allow said elongate support member to extend only across the patient's mouth wherein said at least one aperture and said at least one opening in said first branch and said at least one opening in said second branch located on said first side and are adapted to face towards the patient's mouth.

3. The combination of claim 2 wherein the at least one opening in the first branch is located at a first half section of the support member and wherein the at least one opening in the second branch is located at a second half section of the support member.

4. The combination of claim 2 or 3 wherein the first end and second end of the drape support each comprise an adhesive section capable of adhering to a patient's skin.

5. The combination of claim 4 wherein the oxygen supply hose and carbon dioxide sampling hose are attached to the support member by extending said hoses through at least one aperture within said support member.

6. The combination of claim 2 or 3 further comprising a flap extending from an elongate edge of the support member, said flap being capable of folding towards the chin of a patient when said support member is attached across the mouth of a patient.

7. The combination of claim 2 or 3 wherein said drape support comprises non-corrugated cardboard.

8. The combination of claim 2 or 3 further comprising a tab located on the second side of the support member at a central portion thereof.

9. The drape support of claim 1 or 2 wherein the support member comprises an elongate bendable material.

* * * * *